United States Patent [19]
Tomita et al.

[11] Patent Number: 5,211,830
[45] Date of Patent: May 18, 1993

[54] SHEET-TYPE ELECTRODE FOR USE IN THE MEASUREMENT OF ION CONCENTRATION

[75] Inventors: Katsuhiko Tomita, Otsu; Masami Nakane, Kyoto; Yoko Ogihara, Muko, all of Japan

[73] Assignee: Horiba, Ltd., Kyoto, Japan

[21] Appl. No.: 676,847

[22] Filed: Mar. 28, 1991

[30] Foreign Application Priority Data

Apr. 2, 1990 [JP] Japan .................................. 2-87656

[51] Int. Cl.⁵ .......................................... G01N 27/26
[52] U.S. Cl. .................................... 204/416; 204/419
[58] Field of Search ....................... 204/416, 418, 419

[56] References Cited

U.S. PATENT DOCUMENTS

| | | | |
|---|---|---|---|
| 3,835,011 | 6/1972 | Baum et al. | 204/418 |
| 4,059,499 | 11/1977 | Ibsen Nielsen et al. | 204/418 |
| 4,797,188 | 1/1989 | Tomita | 204/419 |

Primary Examiner—John Niebling
Assistant Examiner—Bruce F. Bell
Attorney, Agent, or Firm—Price, Gess & Ubell

[57] ABSTRACT

A sheet-type, highly polymerized composite electrode used for measuring ionic concentration includes a thin film ion-selective responsive membrane formed on an upper surface of an insulating support layer by sequentially dripping an ion-selective responsive membrane paste containing solvent onto the support layer. The ion-selective responsive paste has a polymerization degree sufficient to provide an enduring ion-responsive membrane without any reinforcing structure.

7 Claims, 2 Drawing Sheets

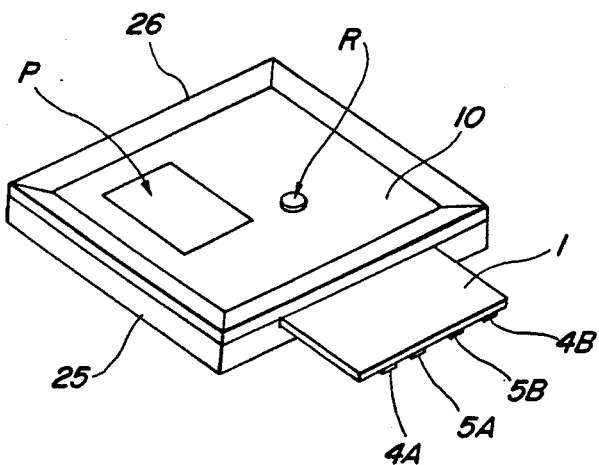
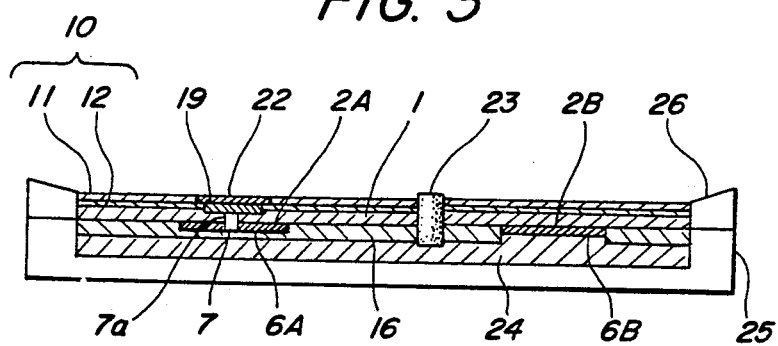
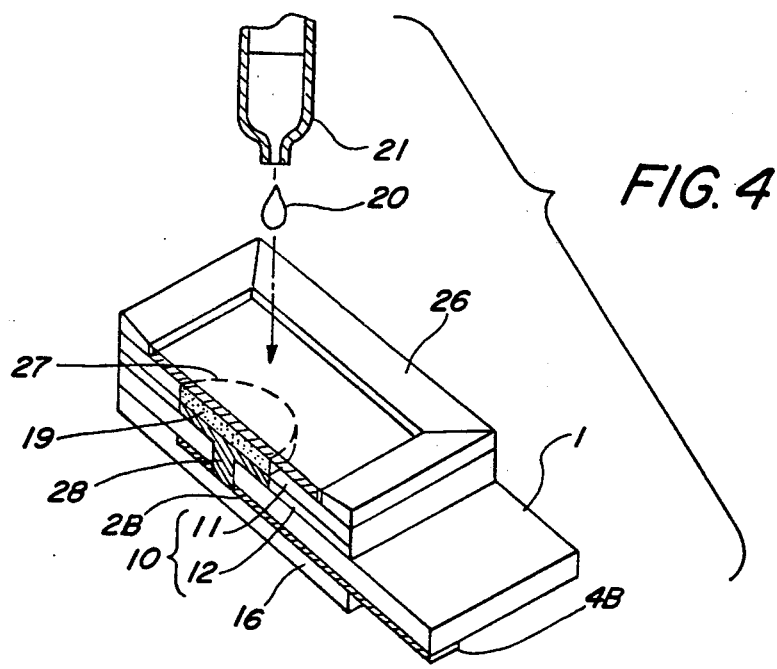

SHEET-TYPE ELECTRODE FOR USE IN THE MEASUREMENT OF ION CONCENTRATION

FIELD OF THE INVENTION

The present invention relates to the measurement of pH or ion concentrations in a sample and, more specifically, to a sheet-type electrode apparatus for measuring a sample's ionic concentration.

BACKGROUND OF THE INVENTION

In conventional sheet-type electrode devices for measuring ion concentrations, as disclosed in Japanese Patent Application Laid-Open No. Sho 63-225164, a thin film ion-selective responsive membrane is formed on an upper surface of an insulating support layer. The membrane is formed by dripping an ion-selective responsive membrane paste, containing a solvent, upon the upper surface of the insulating support layer. The solvent may be polyvinyl chloride resin powders, to which the insulating support layer is soluble, and an ion-responsive substance.

In such prior art sheet-type electrodes, the ion-selective responsive membrane is capable of sealing against the support layer and being formed within a short time. This advantage allows mass production, but problems have occurred.

Due to the fact that the sample to be measured is liquid in many cases, the responsive membrane becomes swollen and deteriorates after repeated measurements. The surface of the responsive membrane is wiped with materials such as gauze when the membrane is used as a sheet-type electrode to measure ions. Wiping the surface of the responsive membrane also causes the membrane to become deformed or substantially worn when rubbed hard.

Attempts have been made to strengthen the ion-selective responsive membrane by adding reinforcing materials, such as a nylon mesh or other inorganic material, in the formation of the responsive membrane. This addition of a reinforcing material to the responsive membrane has resulted in the reinforcing material projecting from the surface of the responsive membrane while the responsive membrane is being used. These projections cause insulating fractures, and thereby reduce accuracy.

OBJECTS OF THE INVENTION

It is therefore an object of the present invention to provide an improved sheet-type electrode used in the measurement of ionic concentration of a sample;

It is another object of the present invention to provide a sheet-type electrode that does not become swollen after repeated uses;

It is yet a further object of the present invention to provide a sheet-type electrode that does not become deformed or worn when repeatedly rubbed; and It is yet a still further object of the present invention to provide a sheet-type electrode which does not use reinforcing materials which reduce testing accuracy.

SUMMARY OF THE INVENTION

These and other objects and advantages are achieved by providing a sheet-type electrode used in the measurement of ionic concentration in which a thin-film ion-selective responsive membrane is formed on an upper surface of an insulative support layer. The membrane is formed on the insulative support layer by sequentially disbursing drops of a selective responsive membrane paste.

In the preferred embodiment, the paste includes polyvinyl chloride resin powders, having a polymerization degree of not less than 3,799 and not greater than 20,001, onto the support layer. The membrane paste may also contain a solvent to which the insulating support layer is soluble. The insulative support layer may include an ion-responsive substance.

The ion-selective responsive membrane of the present invention, when formed by the polymerized polyvinyl chloride resin powders, results in a high-density responsive membrane having substantially less swelling than conventional ion-selective responsive membranes and improved abrasion resistance.

BRIEF DESCRIPTION OF THE DRAWINGS

The present invention, both as to its organization and manner of operation, together with further objects and advantages, may be understood by reference to the following drawings.

FIG. 2 is a perspective view of the constructed preferred embodiment of the present invention;

FIG. 3 is a cross-sectional view showing the sheet-type electrode of the preferred embodiment; and FIG. 4 is a partially cutaway perspective view of an alternative embodiment of the present invention.

DESCRIPTION OF THE PREFERRED EMBODIMENTS

Figure 1:
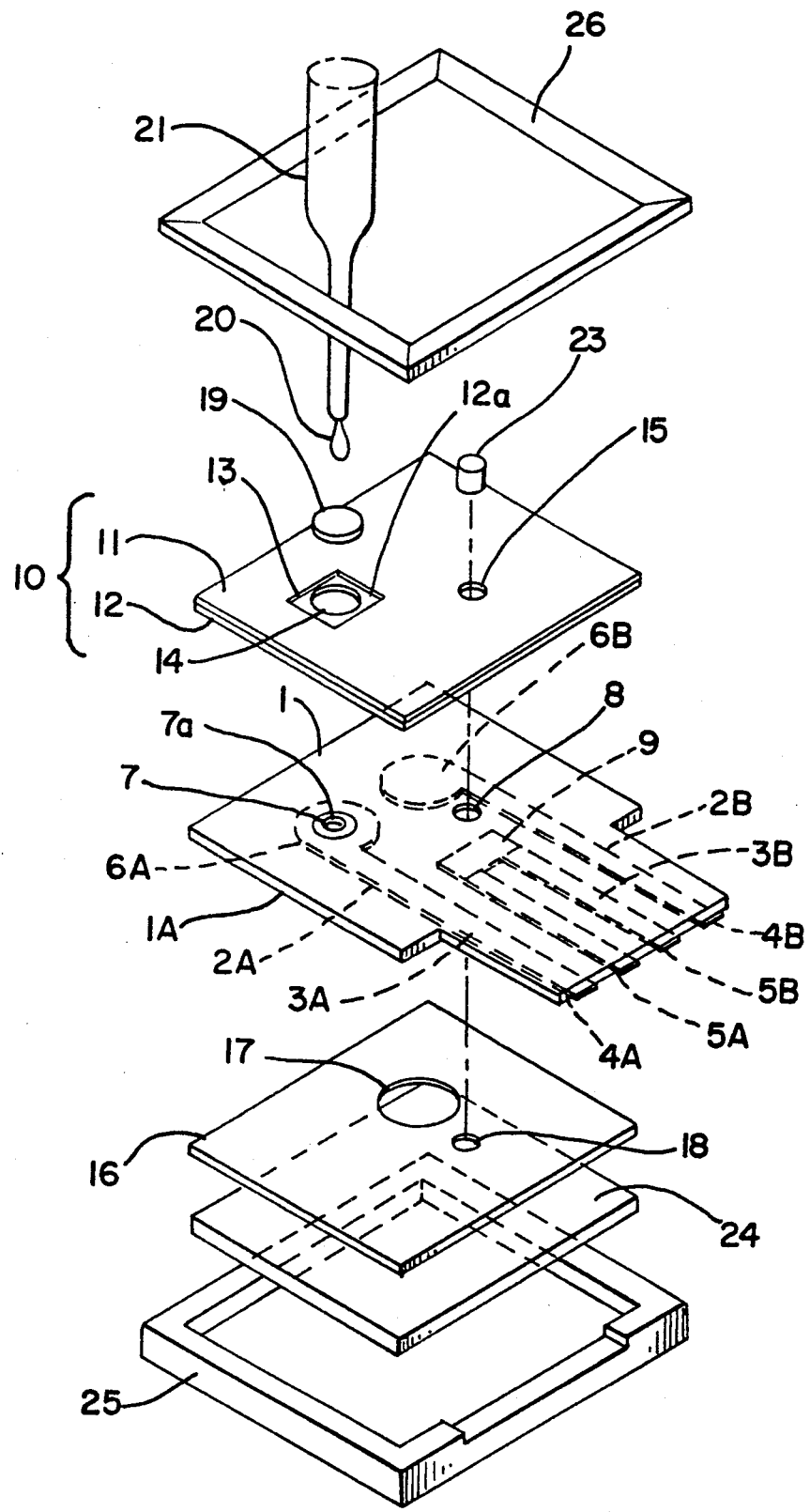
FIG. 1 is an exploded perspective view of a sheet-type electrode constructed according to the preferred embodiment of the present invention.

The following description is provided to enable any person skilled in the art to make and use the invention and sets forth the best modes contemplated by the inventor of carrying out his invention. Various modifications, however, will remain readily apparent to those skilled in these arts, since the generic principles of the present invention have been defined herein.

Referring to FIGS. 1-3, the preferred embodiment of the present invention includes a substrate 1 made of a material that should be insulative, even when immersed in an electrolytic solution. The substrate 1 may be formed of a suitable high molecular organic material such as polyvinyl chloride resin (PVC), polyethylene, polypropylene, acryl, and polyfluoroethylene. The substrate 1 may also be made of inorganic materials such as silica glass, pyrex glass, and polyethylene terephthalate (PET).

Two pairs of electrodes, an outside pair 2A, 2B, and an inside pair 3A, 3B, adhere to a lower surface 1A of the substrate 1. The electrodes 2A, 2B. 3A, 3B may be connected to the substrate's lower surface IA using a physical plating method such as vacuum vapor deposition, or a suitable electrolytic or electroless chemical vapor deposition (CVD). The pairs of electrodes 2A, 2B, 3A, 3B may also be adhered to the substrate 1 using a suitable printing method, such as silk screening relief printing, or the flat plate method.

The pairs of electrodes 2A, 2B, 3A, 3B are made of a conductive metal alloy that may be selected from metals such as Ag, Cu, Au, and Pt, or a paste containing such metals. The electrodes 2A, 2B, 3A. 3B may also be fabricated from a suitable semiconductor such as $IrO_2$ or $SnO_2$. The preferred embodiment, the substrate's lower surface 1A undergoes a grafting process and an anchoring treatment using a coupling agent such as silane, followed by forming an Ag paste using silk screening on the lower surface 1A.

The pairs of electrodes 2A, 2B, 3A, 3B have ends 4A, 4B, 5A, 5B which are used as leads, as discussed below. The outside pair of electrodes 2A, 2B include circular end portions located in the substrate 1 to form internal circular electrodes 6A, 6B. The circular electrodes 6A, 6B may be coated with a suitable electrode material, such as AgCl. A hole 7 is disposed through the center portion of one circular internal electrode 6A. The hole 7 has an electrically conductive sleeve 7A disposed about its periphery. A hole 8 is disposed through the substrate 1 adjacent to the periphery of the internal electrode 6B. A temperature-compensating device 9, such as a thermistor, extends over ends of the inside electrodes 3A, 3B distal to the leads 5A, 5B.

An insulating support layer 10 may be fabricated using an upper sheet metal 11 and a lower sheet material 12. In this embodiment, the upper sheet material 11 may be made of PET, and the lower sheet material 12 may be made of PCV. The sheet materials 11, 12 should have a substantially high insulative value relative to one another. The support layer 10 is fabricated by splicing adjacent sides of the sheet materials 11, 12. The sheet materials 11, 12 undergo a surface treatment processing such as printing using an ultraviolet setting ink, semi-drying, then pressing both sheet materials 11, 12 together to form the support layer 10.

The lower sheet 12 has a circular opening 14 disposed therethrough, while the upper sheet 11 has a square opening 13 disposed therethrough directly above the circular opening 14. The square opening 13 provides access to a treated side 12A of the lower sheet 12. The openings 13, 14 are disposed through the support layer 10 in substantial alignment with the hole 7 in the substrate 1. An additional hole 15 is disposed through the support layer 10 and aligned with the substrate's second hole 8. An exterior side of the upper sheet 11 undergoes a grafting process and anchoring treatment similar to that performed on the substrate.

A lower support layer 16 made of an insulative material having a high insulative value similar to that of the substrate 1, such as PET, is provided on a lower surface of the substrate 1. The lower support layer 16 may be fabricated in the same manner as the support layer 10. A substantially large circular opening 17 is disposed through the lower support layer 16 and in substantial alignment with the circular internal electrode 6B. A substantially small opening 18 is located adjacent to the large opening 17 and in alignment with the hole 8 in the substrate.

A disk-like membrane 19 may be made from a suitable gelatinized internal liquid. The gelatinized internal liquid may be made of a suitable glycerine-agar-agar ($0.03M$-$KNO_3$—$0.1M$-$KCl$) compound. The disk-like membrane 19 is placed in the lower sheet's circular opening 14 using silk screen printing. The disk-like membrane 19 is transformed into a paste by heating. The heated paste membrane 19, when placed in the opening 14, has an upper surface slightly below the exterior of the sheet material 11 and extends through the circular opening 14, for adhering to the internal electrode 6A via the hole's electrically conductive inner sleeve 7A.

An ion-selective responsive paste 20 is disposed on the disk-like membrane 19 using sequential drops for forming an ion-selective responsive membrane. In the preferred embodiment, the ion-responsive paste 20 is obtained by dissolving 0.5 g of PVC powders, as an $NO_3$-responsive substance, and 0.166 g of di-n-octyl phthalate, as a plasticizer, in 10 ml of tetrahydrofuran (THF), which is a solvent. In this embodiment, the PVC powders have a polymerization degree of substantially 3,800 to 20,000, 0.333 g of suitable nitrate-type quaternary ammonium salts ($RNNO_3$, R: $C_8$ to $C_{17}$), such as tetraoctylammonium nitrate, trioctylmethylammonium nitrate, and tetradodecylammonium nitrate. An ion-responsive paste 20, composed using the given contents and the described procedure, forms an ion-responsive membrane which does not swell and is substantially wear-resistant.

The ion-responsive paste 20 is put in a syringe 21 and disbursed sequentially in drops of an appropriate quantity onto the disk-like membrane 19. After the desired amount of ion-responsive paste 20 is disbursed onto the disk-like membrane 19, the paste 20 is evaporated until dry. An $NO_3$- responsive membrane 22 having a thickness of approximately 20 microns is formed by repeating the above-described process multiple times.

The viscosity of the ion-responsive paste 20 may be increased by increasing the polymerization degree of the PVC powders. The number of repetitions of the described process and the quantity of ion-responsive paste 20 to be disposed should be regulated in the application of the paste to the disk-like membrane 19 so that the desired film thickness is achieved. This may be done by increasing the quantity of THF in the ion-responsive paste 20.

A cylindrical member 23 functions as a liquid electrical junction for a reference electrode R, and is inserted through openings 15, 8, and 18 The cylindrical member 23 consists of a gel-impregnated hydrophilic, high molecular porous member 23 which may be made of a sintered molded body fabricated from the olefin family of high polymer powders, such as SUN FINE AQ made by Asahi Kasei KK, Japan. The cylindrical member 23 has a mechanical strength similar to that of polyoelfines, and a hydrophilicity achieved by a denaturing treatment, the member 23 being impregnated with a drying out gel composite.

The gel composite may comprise a water-saturated compound jelly containing an Na salt and an acrylic polymer. The gel composite is commercially available under the trade name U JELLY, manufactured by Showa Denko KK, Japan. The gelatine composite does not deposit KCl on the support layer 10, and does not lose wetness on the surface of the cylindrical member 23. The length of the cylindrical member 23 is such that it extends completely through the lower support layer 16 and the substrate 7, and projects slightly above the upper sheet 11.

A gelatinized internal liquid 24 having substantially the same chemical composition as that of the disk-like membrane 19 is adapted to be brought into contact with the internal electrode 6B through the lower support layer's substantially large hole 17. The internal liquid 24 is further brought into contact with the cylindrical member 23. A bottom case 25 and holder 26 are used to sandwich the support member 10, substrate 1, lower support layer 16, and internal liquid 24, and to retain them in a fixed relationship.

FIG. 4 shows an ion-responsive membrane electrode embodying the present invention. An ion-selective responsive membrane 27 is formed by solidifying the ion-responsive paste 20. A cylindrical electrode 28, formed through the substrate 1, connects the disk-like membrane 19 with the electrode's lead 2B.

The present invention may also be applied to PVC family liquid membrane-type ion-selective electrode-measuring materials such as $Na^+$, $K^+$, $Cl^-$, $Ca^{++}$, and $H^+$, respectively. The compositional ratio (% by weight) which may be used in the respective ion electrodes is shown in the following table:

TABLE

|  | $Na^+$ | $K^+$ | $Cl^-$ | $Ca^{++}$ | $H^+$ |
| --- | --- | --- | --- | --- | --- |
| PVC powders | 32 | 32 | 50 | 26.5 | 50 |
| Responsive substance | 3.2 | 3.2 | 33.3 | 6.7 | 33.3 |
| Plasticizer | 64 | 64 | 16.6 | 66.8 | 16.6 |
| Others | 0.8 | 0.8 | — | — | — |

Other responsive substances that may be used in the present invention and which are not listed in the table may be: $B_{is}$-12-Crown-4 for $Na^+$; barinomycin for $K^+$; trioctylmethylammonium chloride for Cl.; Ca-di-(p-octylphenyl) phosphate for $Ca^{++}$; and trioctylphosphine oxide for $H^+$.

In the above-described $NO_3^-$ measuring sheet-type composite electrode, highly polymerized polyvinyl chloride resin powders are used in the formation of ion-selective responsive membranes. The high density responsive membrane formed has improved abrasion resistance and does not deteriorate from slowing. The responsive substance dissolved in the plasticizer is effectively prevented from eluting so that a high capacity sheet-type electrode for use in measuring of ions is obtained. The relative ease of the present invention lends itself to mass production of sheet-type electrodes used in the measurement of ions.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved sheet-type electrode for use in a measurement of ionic concentration, comprising:
    an ion-selective responsive membrane including polyvinyl chloride resin powder having a polymerization degree not less than 3,799 and not greater than 20,001.

2. The improved sheet-type electrode of claim 1 wherein the polyvinyl chloride resin powder includes polyvinyl chloride powder having a polymerization degree of not less than 3,799 and not greater than 20,001 dissolved by a nitrate-type quaternary ammonium salt and a plasticizing compound comprising di-n-octyl phthalate, and a solvent comprising tetrahydrofuran.

3. The improved sheet-type electrode of claim 2 wherein the nitrate-type quaternary ammonium salt is selected from the group consisting of tetraoctylammonium nitrate, trioctylmethylammonium nitrate, and tetradodecylammonium nitrate.

4. The sheet-type electrode of claim 3 wherein there is substantially 0.5 grams of polyvinyl chloride powder, substantially 0.333 grams of nitrate-type quaternary ammonium salt, 0.166 grams of plasticizer, and substantially 10 milliliters of solvent in the polyvinyl chloride powder.

5. A sheet-type electrode for measuring ionic concentration, comprising:
    an insulating support layer having an upper surface and a lower surface, the upper surface of the insulating support layer comprising an ion-responsive substance that is soluble; and
    a thin-film ion-selective responsive membrane disposed on the upper surface containing a solvent, the ion-selective responsive membrane being formed by polyvinyl chloride resin having a polymerization degree of not less than 3,799 and not greater than 20,001.

6. The sheet-type electrode of claim 5, wherein the ion-selective responsive membrane is formed on the upper surface of the insulating support layer by sequentially disbursing drops of an ion-selective responsive membrane paste of a desired amount onto the insulating support layer.

7. A sheet-type electrode for receiving a liquid sample and measuring the sample's ionic concentration, the electrode being deposited upon an insulating support layer as an ion-responsive membrane paste, the paste being sufficiently polymerized to provide a nonreinforced thin-film ion-selective responsive membrane capable of enduring multiple measurements.

* * * * *